(12) United States Patent
Portnoy

(10) Patent No.: US 9,984,208 B2
(45) Date of Patent: *May 29, 2018

(54) MEDICAL EMERGENCY FRAMEWORK

(71) Applicant: CERNER INNOVATION, INC., Kansas City, KS (US)

(72) Inventor: Alan Mark Portnoy, Warminster, PA (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/388,895

(22) Filed: Dec. 22, 2016

(65) Prior Publication Data

US 2017/0103170 A1    Apr. 13, 2017

Related U.S. Application Data

(63) Continuation of application No. 14/476,840, filed on Sep. 4, 2014, now Pat. No. 9,594,873.

(51) Int. Cl.
| | |
|---|---|
| G06Q 30/00 | (2012.01) |
| G06Q 90/00 | (2006.01) |
| G06F 19/00 | (2018.01) |
| G06K 7/10 | (2006.01) |

(52) U.S. Cl.
CPC ....... *G06F 19/327* (2013.01); *G06K 7/10297* (2013.01); *G16H 10/60* (2018.01); *G16H 40/20* (2018.01)

(58) Field of Classification Search
CPC .. G06F 19/322; G06F 19/327; G06F 19/3462; G06K 7/10297; G06Q 10/08; G06Q 10/087; G06Q 50/22; A61G 12/011; A61G 2205/20; A61G 2205/60

See application file for complete search history.

(56) References Cited

U.S. PATENT DOCUMENTS

| | | |
|---|---|---|
| 5,696,365 A | 12/1997 | Ukai et al. |
| 6,283,647 B1 | 9/2001 | Konishi et al. |
| 6,655,545 B1 * | 12/2003 | Sonneborn ............ G06F 19/325 221/7 |
| 7,230,529 B2 | 6/2007 | Ketcherside, Jr. et al. |
| 7,278,579 B2 | 10/2007 | Loffredo et al. |
| 7,703,682 B2 | 4/2010 | Kenney |
| 7,708,198 B2 | 5/2010 | Gangi |
| 7,712,658 B2 | 5/2010 | Gangi |
| 7,967,190 B2 | 6/2011 | Hussey |
| 2002/0132585 A1 | 9/2002 | Palermo et al. |
| 2002/0161708 A1 | 10/2002 | Offer |

(Continued)

Primary Examiner — Laura Gudorf
(74) Attorney, Agent, or Firm — Shook, Hardy & Bacon, L.L.P.

(57) ABSTRACT

Disclosed herein is a framework for facilitating a medical emergency workflow. In accordance with one aspect, a code cart is paired with a computer system. The code cart may include tracking tags attached to the code cart and cart items. The computer system may include a data collector for scanning the tracking tags and an application. The application may be executable by a processor to perform steps including receiving, from the data collector, information associated with the code cart and one or more selected cart items, and updating a medical emergency record based at least in part on the received information.

20 Claims, 3 Drawing Sheets

(56) References Cited

U.S. PATENT DOCUMENTS

| | | |
|---|---|---|
| 2003/0144035 A1 | 7/2003 | Weinblatt et al. |
| 2004/0010425 A1 | 1/2004 | Wilkes et al. |
| 2004/0021693 A1 | 2/2004 | Monteleone |
| 2004/0078231 A1 | 4/2004 | Wilkes et al. |
| 2004/0172283 A1 | 9/2004 | Vanderveen et al. |
| 2004/0172300 A1 | 9/2004 | Mihai et al. |
| 2004/0199405 A1 | 10/2004 | Harper et al. |
| 2004/0204910 A1 | 10/2004 | Brumbach et al. |
| 2005/0021368 A1 | 1/2005 | Burkeen et al. |
| 2005/0101844 A1 | 5/2005 | Duckert et al. |
| 2005/0277872 A1 | 12/2005 | Colby et al. |
| 2006/0026205 A1 | 2/2006 | Butterfield |
| 2006/0106647 A1 | 5/2006 | Brummel et al. |
| 2006/0106648 A1 | 5/2006 | Esham et al. |
| 2006/0149416 A1 | 7/2006 | Mahapatra et al. |
| 2006/0184160 A1 | 8/2006 | Ozaki et al. |
| 2007/0033075 A1 | 2/2007 | Hoffman et al. |
| 2007/0088458 A1 | 4/2007 | Laughland et al. |
| 2007/0168223 A1 | 7/2007 | Fors et al. |
| 2008/0011825 A1 | 1/2008 | Giordano et al. |
| 2008/0017722 A1 | 1/2008 | Snyder et al. |
| 2008/0028214 A1 | 1/2008 | Tafoya et al. |
| 2008/0065424 A1 | 3/2008 | Frick |
| 2008/0082366 A1 | 4/2008 | Miller et al. |
| 2008/0097792 A1 | 4/2008 | Marge |
| 2008/0189170 A1 | 8/2008 | Ramachandra |
| 2008/0198028 A1 | 8/2008 | Watanabe |
| 2008/0261526 A1 | 10/2008 | Suresh |
| 2009/0037515 A1 | 2/2009 | Zapata et al. |
| 2009/0112072 A1 | 4/2009 | Banet et al. |
| 2009/0138286 A1 | 5/2009 | Linder et al. |
| 2009/0164238 A1 | 6/2009 | Auchinleck |
| 2009/0222746 A1 | 9/2009 | Chirica et al. |
| 2009/0267772 A1* | 10/2009 | Dehnadi ............ A61G 12/001 340/572.8 |
| 2010/0001838 A1 | 1/2010 | Miodownik et al. |
| 2010/0012715 A1 | 1/2010 | Williams et al. |
| 2010/0038417 A1 | 2/2010 | Blankitny |
| 2010/0063847 A1 | 3/2010 | Eisenberg et al. |
| 2010/0065634 A1 | 3/2010 | Nakamura |
| 2010/0169120 A1 | 7/2010 | Herbst et al. |
| 2010/0169121 A1 | 7/2010 | Herbst et al. |
| 2010/0219242 A1 | 9/2010 | Gangi |
| 2010/0230485 A1 | 9/2010 | Kenney |
| 2010/0241456 A1 | 9/2010 | Miller et al. |
| 2010/0271208 A1 | 10/2010 | Steinmetz et al. |
| 2011/0072263 A1 | 3/2011 | Bishop et al. |
| 2011/0081860 A1 | 4/2011 | Brown et al. |
| 2011/0101115 A1 | 5/2011 | Rampersad |
| 2011/0131061 A1 | 6/2011 | Shain |
| 2011/0210170 A1 | 9/2011 | Arguello |
| 2011/0297747 A1 | 12/2011 | Naumovsky |
| 2011/0302051 A1 | 12/2011 | Arbatli |
| 2011/0313870 A1 | 12/2011 | Eicher et al. |
| 2012/0029303 A1 | 2/2012 | Shaya |
| 2012/0041782 A1 | 2/2012 | Morris |
| 2012/0072536 A1 | 3/2012 | Xu et al. |
| 2012/0179908 A1 | 7/2012 | Duma |
| 2012/0205441 A1 | 8/2012 | Utech et al. |
| 2013/0013548 A1 | 1/2013 | Alexander et al. |
| 2013/0185092 A1 | 7/2013 | Dubbels et al. |
| 2014/0288947 A1 | 9/2014 | Simpson et al. |
| 2015/0106114 A1 | 4/2015 | Ramsey et al. |
| 2015/0227885 A1 | 8/2015 | Zini et al. |

* cited by examiner

MEDICAL EMERGENCY FRAMEWORK

CROSS-REFERENCE TO RELATED APPLICATIONS

This application is a continuation of co-pending U.S. patent application Ser. No. 14/476,840, filed Sep. 4, 2014, and titled "Medical Emergency Framework," the entire contents of which are incorporated herein by reference in their entirety.

TECHNICAL FIELD

The present disclosure generally relates to a medical emergency framework.

BACKGROUND

When a "Code Blue" (also known as "code") is called within a hospital, it indicates that a patient is in a life threatening state and requires immediate treatment. In many instances, treatment is administered according to a hospital life support protocol or guidelines, such as the Advanced Cardiac Life Support (ACLS) algorithm. From an operational perspective, a specially stocked code cart (also known as a crash cart or trolley) is moved to the patient's bedside. The code cart is a set of trays, drawers, shelves, etc., on wheels that is used to transport and dispense emergency medication and equipment for Code Blue resuscitations to potentially save a patient's life. Documentation during the medical emergency is commonly performed manually on a separate Code Blue paper document. Once the Medical emergency has been concluded, the code cart must be cleaned and re-stocked. This usually involves the Pharmacy and Central Supply Departments physically removing the cart from the nursing unit. Since the nursing unit must always have a crash cart, a new fully stocked cart is delivered to the nursing unit.

"Code Blue" events are very stressful situations that require quick reactions to patient conditions that can change in an instant. Although barcode technology can be used to reduce errors in identification and management of medications, the workflow associated with typical Bar Code Medication Administration (BCMA) applications has proven to be too time-consuming to allow for use during medical emergencies. Incorporating BCMA into a medical emergency workflow is very difficult due to the time consuming, multi-step process that is required in a BCMA application to ensure the six rights of medication administration.

In addition, using clinical decision support tools to monitor and advise a clinician during a Medical emergency has been almost impossible due to the fast-paced workflow that is common in this life-and-death situation. For these reasons, many hospitals manage Code Blue documentation on paper. Data received from medical equipment (e.g., electrocardiogram or EKG monitors, ventilators, defibrillators, etc.) are typically not integrated into the code blue record. Other systems have attempted to provide some level of automation to the Code Blue process, but does not provide any data integration or decision support capabilities.

SUMMARY

The present disclosure relates to a framework for facilitating a medical emergency workflow. In accordance with one aspect, a code cart is paired with a computer system. The code cart may include tracking tags attached to the code cart and cart items. The computer system may include a data collector for scanning the tracking tags and an application. The application may be executable by a processor to perform steps including receiving, from the data collector, information associated with the code cart and one or more selected cart items, and updating a medical emergency record based at least in part on the received information.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
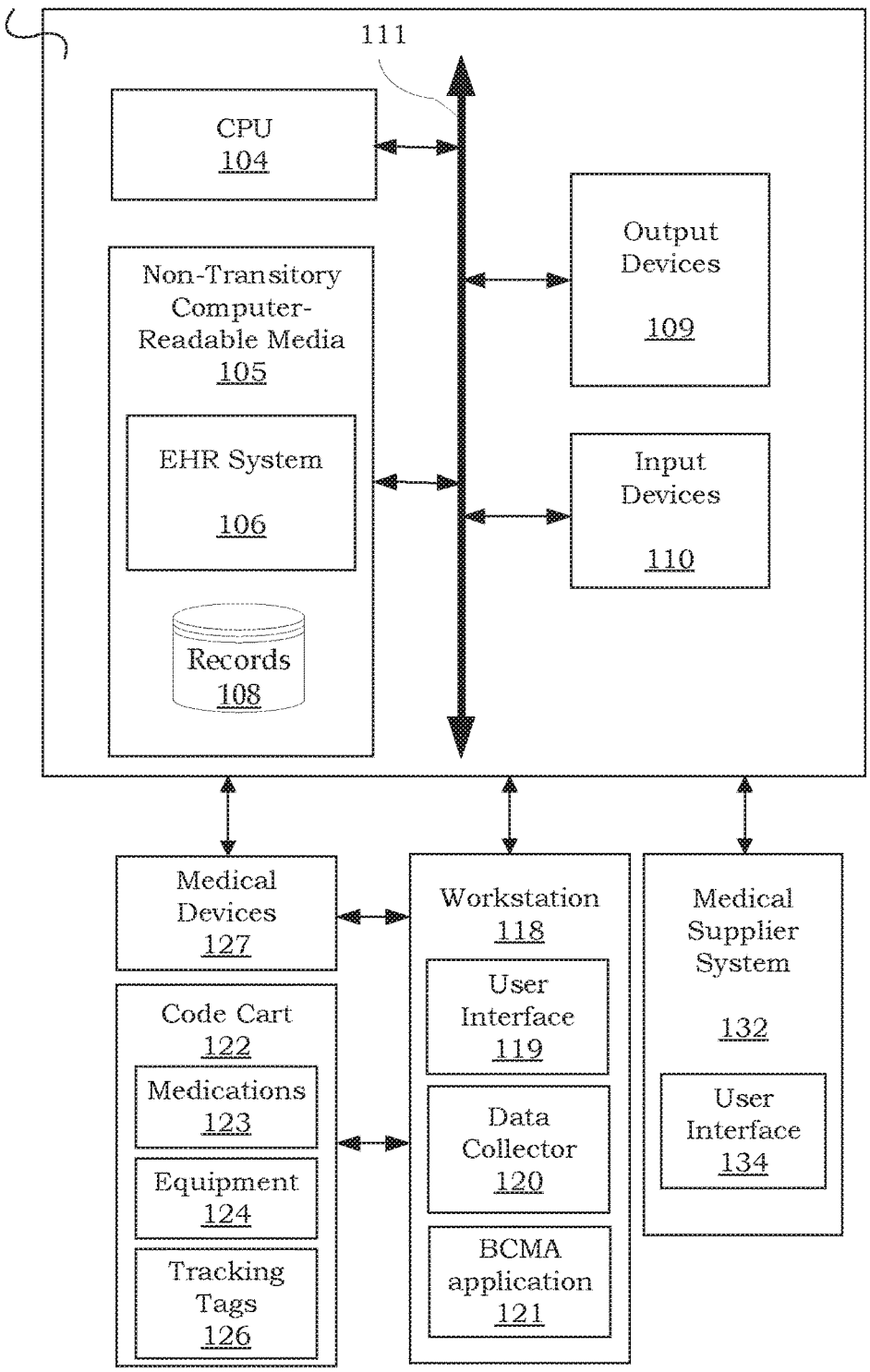
FIG. 1 is a block diagram illustrating an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

Unless stated otherwise as apparent from the following discussion, it will be appreciated that terms such as "generating," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system's memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

A framework for facilitating a medical emergency workflow is described herein. In accordance with one aspect of the framework, a code cart logistical workflow is integrated with a data collection system that provides an easy method to capture medication administration and intervention information during a medical emergency (or code event). Such data collection system may be a Bar Code Medication Administration (BCMA) system that provides the benefits of barcoding and/or radio-frequency identification (RFID) Bluetooth tracking to quickly identify and document administered medications, events and interventions that occur during the medical emergency.

Synchronizing the code cart with the data collection system provides many logistical benefits, such as inventory management, charge capture, location tracking, re-stocking, purchase order (PO) generation, invoicing, etc. In addition, clinical decision support tools may be used to advise and recommend interventions and/or treatments during the medical emergency. Independent BCMA visual image confirmation of the code cart item's identity, in addition to barcode scanning, ensures correct medications are administered and therefore patient safety. All medications administered and data received from medical devices during the medical emergency may be easily documented. Decision support may be provided to monitor compliance with clinical protocols. Medical device integration may be provided so that data captured during a medical emergency may be merged into a single complete time-based record of the entire event. These and other exemplary advantages and features will be described in further details in the following description.

FIG. 1 is a block diagram illustrating an exemplary system 100. The system 100 includes a computer system 101 for implementing the framework as described herein. The computer system 101 may further be connected to a workstation 118, medical devices 127 and a medical supplier system 132 over a wired or wireless communication network (e.g., local area network, wide area network, etc.). Depending upon the context, workstation 118 and medical supplier system 132 may be called client devices and the computer system 101 may be referred to as the server. Although an exemplary client-server architecture is shown, it should be appreciated that other configurations are also possible.

Computer system 101 may be a desktop personal computer, a portable laptop computer, another portable device, a mini-computer, a mainframe computer, a server, a storage system, a dedicated digital appliance, or another device having a storage sub-system configured to store a collection of digital data items. In one implementation, computer system 101 comprises a processor or central processing unit (CPU) 104 coupled to one or more non-transitory computer-readable media 105 (e.g., computer storage or memory), output devices 109 (e.g., monitor, display, printer, etc.) and various input devices 110 (e.g., mouse, keyboard, touch pad, voice recognition module, etc.) via an input-output interface 111. Non-transitory computer-readable media 105 may include random access memory (RAM), read only memory (ROM), magnetic floppy disk, flash memory, and other types of memories, or a combination thereof. Computer system 101 may further include support circuits such as a cache, a power supply, clock circuits and a communications bus (not shown). Various other peripheral devices, such as additional data storage devices and printing devices, may be connected to the computer system 101.

It is to be understood that the present technology may be implemented in various forms of hardware, software, firmware, special purpose processors, or a combination thereof. In one implementation, the techniques described herein are implemented in an electronic health record (EHR) system 106 and an integrated BCMA application 121 implemented on workstation 118. Alternatively, the BCMA application 121 may be a standalone application in workstation 118.

EHR system 106 serves to systematically collect, organize and store electronic health information, including any information associated with a medical emergency and code cart data, about an individual patient or population in records database 108. BCMA application 121 is a data collection application that serves to facilitate a workflow associated with a medical emergency, and is synchronized with a code cart 122, as will be described in more details later.

EHR system 106 and BCMA application 121 may include computer-readable program code tangibly embodied in non-transitory computer-readable media. The computer-readable program code is executed by a processor (e.g., CPU 104). The computer-readable program code is not intended to be limited to any particular programming language and implementation thereof. It will be appreciated that a variety of programming languages and coding thereof may be used to implement the teachings of the disclosure contained herein. Computer system 101 may also include an operating system and microinstruction code. The various techniques described herein may be implemented either as part of the microinstruction code or as part of an application program or software product, or a combination thereof, which is executed via the operating system.

The workstation 118 may include a computer system with components similar to computer system 101, such as a processor, non-transitory computer-readable media, output and input devices, and can be operated in conjunction with the entire system 100. The workstation 118 is communicatively coupled or paired to a mobile code cart 122 via a wired or wireless network (e.g., cellular wireless communication, Bluetooth wireless communication, universal serial bus or USB, etc.). For example, the workstation 118 may be a Bluetooth device that is paired to the code cart 122 over a wireless Bluetooth connection. As another example, the workstation may be a Universal Serial Bus (USB) device that is paired to the code cart 122 over a physical connection, such as a USB port physically coupled to the workstation 118.

The workstation 118 may further include a user interface 119 that allows a nurse or any other skilled user (e.g., physician, technician, operator, scientist, etc.) to access the functionalities, services and/or data provided by the BCMA application 121 and/or EHR system 106. The workstation 118 may further include a data collector 120 that captures data from, for example, tracking tags 126 physically attached to the code cart 122 or cart items (e.g., medications 123, equipment 124, etc.) The data collector 120 may include, for instance, a radio-frequency identification (RFID) reader, a barcode scanner, camera, other types of data acquisition devices, or a combination thereof. The captured data may then be communicated to the computer system 101 for further processing.

The code cart 122 may include medications 123, equipment 124 and tracking tags 126. In the following description, it should be noted that medications 123 and equipment 124 may be referred to as "cart items" or "cart contents". The types of medications 123 and equipment 124 within the code cart 122 may be standardized according to a particular protocol or guidelines. The contents in the code cart 122 may also vary according to each particular hospital or specialty (e.g., pediatrics). The medications 123 may include, but are not limited to, advanced cardiac life support (ACLS) drugs (e.g., epinephrine, atropine, amiodarone, etc.), drugs for treating common problems, drugs for rapid sequence intubation, and so forth. The equipment 124 may include, but is not limited to, defibrillators, suction devices, bag valve masks, pediatric equipment, surgical tools (e.g., blade), laryngoscope, as well as other types of equipment and supply. Each nursing unit may be provided with at least one code cart 122.

Tracking tags 126 may be physically attached to the code cart 122 and cart items to allow automatic identification and tracking. In some implementations, the tracking tags 126 are radio-frequency identification (RFID) tags. An RFID tag contains electronically stored information (e.g., unique identifier) that can be read, recorded or rewritten by data collector 120 that serves as an RFID reader. Alternatively, or additionally, the tracking tags 126 may be barcodes (e.g., one-dimensional, two-dimensional, Universal Product Code or UPC, etc.) that can be scanned by data collector 120 that serves as a barcode scanner.

Medical devices 127 may include any kind of devices that monitor patient signal data, treat or diagnose patients, including but not limited to, electrocardiogram (EKG) monitors, blood glucose monitors, ventilators, defibrillators, imaging devices, etc. Such medical devices may be located on or outside the code cart 122 (e.g., within the emergency room or intensive care unit). The EHR system 106 and/or the BCMA application 121 may collect, integrate and store data from such medical devices 127 before, during or after the medical emergency.

The medical supplier system 132 may also include a computer system with components similar to computer system 101, such as a processor, non-transitory computer-readable media, output and input devices, and can be operated in conjunction with the entire system 100. The medical supplier system 132 may further include a user interface 134 that allows a pharmacist, supply department or any other skilled user to access the functionalities, services and/or data provided by the EHR system 106.

To set-up or prepare the system 100 for use during medical emergencies, the EHR system 106 may store data of each code cart 122 in the facility (e.g., hospital). Such code cart data may include, but is not limited to, a unique cart identifier (ID), cart location and information associated with cart items (e.g., names, unique identifiers, national drug code or NDC number, quantity, expiration dates, locations within the cart, scanned image or photo, etc.). Tracking tags 126 may be physically attached to each code cart 122 and its individual cart items. Each tracking tag 126 may store a unique identifier (ID) and other information associated with the cart or cart item. When a code cart 122 is sent to a nursing unit or received from a nursing unit, the EHR system 106 may track its physical location by using the information provided by the tracking tag 126. The EHR system 106 may further store clinical protocols used during medical emergencies, such as ACLS algorithms. The EHR system 106 may use such information to recommend interventions and track compliance with protocols. In addition, the EHR system 106 may collect data from medical devices 127 within the clinical environment to consolidate into an electronic medical emergency record.

The EHR system 106 may provide a re-stock mode that allows the user to enter, via user interface 119, the quantity and expiration date (if one is supplied) of each medication 123 within each code cart 122. The EHR system 106 may assign a single expiration date to the code cart 122 to indicate the earliest expiration date of the cart items. Each piece of equipment 124 may also be tagged with a tracking tag 126 (e.g., barcode) and scanned by data collector 120 as it is placed into or removed from the code cart 122. Used equipment 124 that requires cleaning may be tracked to monitor its cleaning status and return to the inventory in the hospital's supply department. Purchase orders may be automatically generated when the quantity of particular disposable equipment 124 reaches critical low par levels. Alternatively, the generation of purchase orders may be initiated by interfacing with the hospital's purchasing system.

The BCMA application 121 may notify the user, via user interface 119, where to place the medication 123 or equipment 124 within the code cart 122 (e.g., which drawer and location within the drawer). The user interface 119 may present a graphical representation of the desired location in the code cart 122 so that the user can visualize the correct placement.

Figure 2:
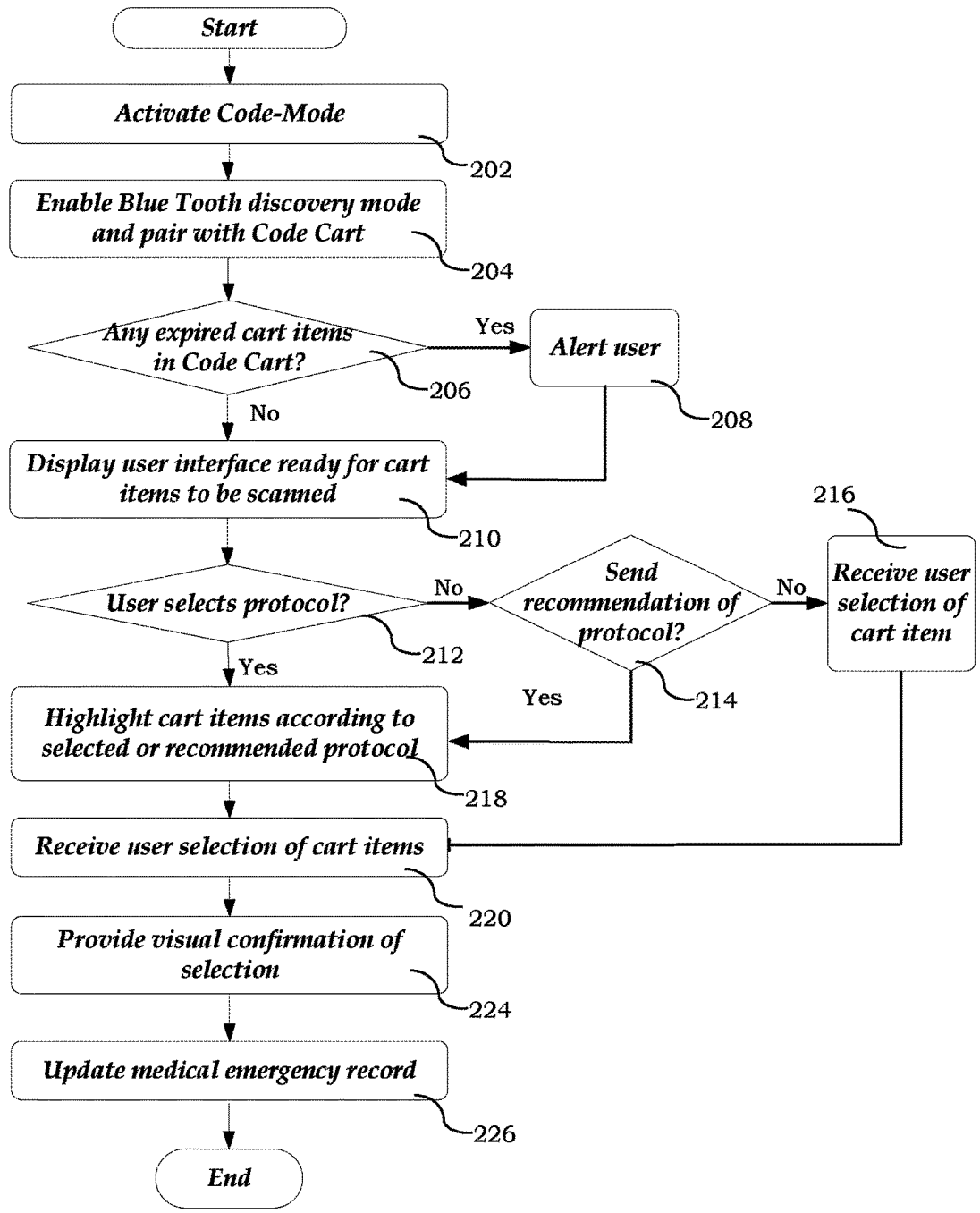
FIG. 2 illustrates an exemplary method of facilitating a medical emergency workflow.

FIG. 2 illustrates an exemplary method 200 of facilitating a medical emergency workflow. It should be noted that the steps of the method 200 may be performed in the order shown or a different order. Furthermore, different, additional or fewer steps may be implemented. Even further, the method 200 may be implemented with the system 100 of FIG. 1, a different system, or a combination thereof.

The method 200 is initiated in response to a medical emergency. The medical emergency generally refers to a situation in which a patient is in immediate need of resuscitation or medical attention, most often as the result of a respiratory arrest or cardiac arrest. Color codes are commonly used to convey essential information regarding the medical emergency quickly and with minimal misunderstanding to staff, while preventing stress and panic among visitors to the hospital. Different terminologies (e.g., "Code Blue", "code", "Plan Blue", "Code Pink", "Code White", etc.) may be used in different hospitals to indicate such medical emergency.

At the start of the medical emergency, a message may be announced over the hospital's public address system to inform hospital staff of the emergency. In response to the medical emergency, a user (e.g., nurse) moves the code cart 122 and a mobile cart with the workstation 118 to the patient's room. The user then logs into the BCMA application via user interface 119. The user may manually enter information about the patient. Alternatively, the user may use a barcode scanner to scan the patient's barcode bracelet to automatically identify the patient. BCMA application 121 may communicate with the EHR system 106 to retrieve the patient's health record. The user may then select a Code-Mode functionality via the user interface 119.

At 202, BCMA application 121 activates the Code-Mode in response to the user selection. When Code-Mode is activated, all data from medical devices 127 connected to the EHR system 106 may be date/time-stamped and flagged as data captured during Code-Mode for integration into the final code record. Once in Code-Mode, the normal (i.e., Non-Code-Mode) BCMA workflow functionality may be disabled until the user exits from the "Code Mode" functionality.

Figure 3:
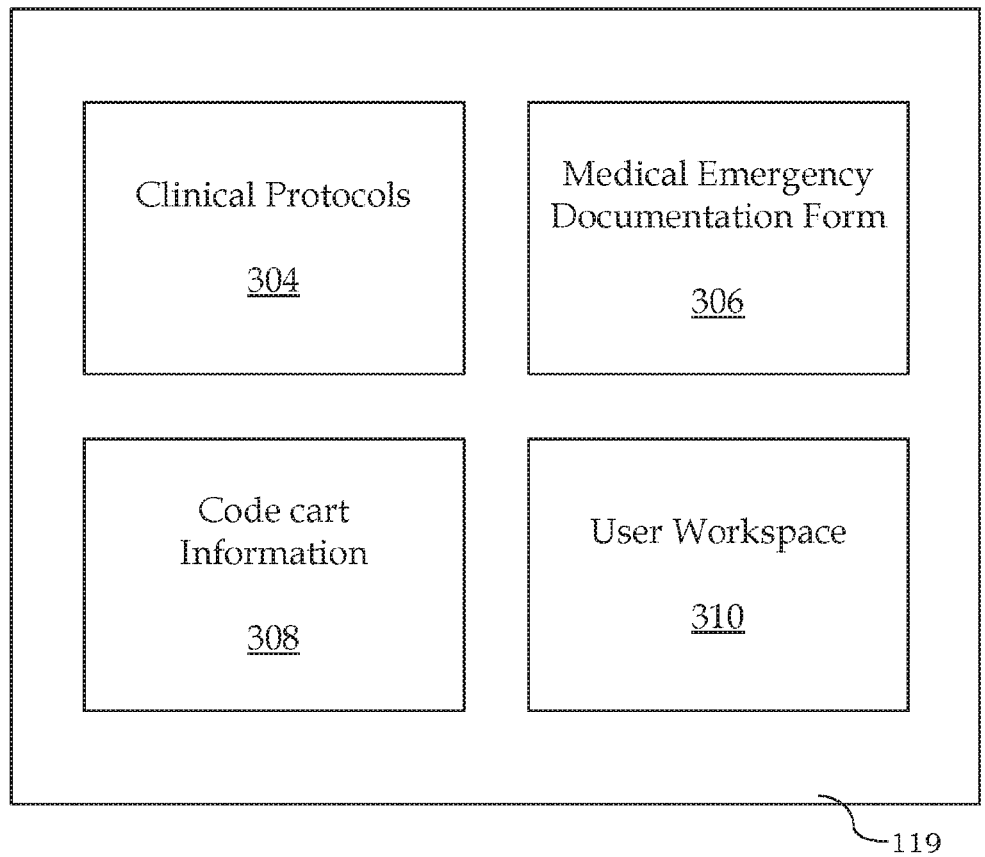
FIG. 3 shows an exemplary user interface.

FIG. 3 shows an exemplary user interface 119 presented by BCMA application 121 in the Code-Mode. As shown, the user interface 119 may include four panels 304-310. First panel 304 may present a pre-defined list of one or more clinical protocols for user selection. One exemplary clinical protocol is the advanced cardiac life support or advanced cardiovascular life support (ACLS) algorithm, which refers to a standardized set of clinical interventions for the urgent treatment of cardiac arrest, stroke and other life-threatening medical emergencies, as well as the knowledge and skills to deploy those interventions. Other types of clinical protocols may also be listed.

Second panel 306 may present a code blue documentation form that provides information from the medical emergency record. The code blue documentation form captures information associated with the current medical emergency. Such information may be associated with, for example, the interventions made during the medical emergency. The interventions may be represented in a chronological view for easy reference during the medical emergency. Such form may be customizable by the user. For example, the user may select the editable fields to be presented in the form.

Third panel 308 may present information associated with the code cart 122, such as a list or graphical representation of the code cart's contents and their respective physical locations within the cart 122. The user may select certain cart items, and the third panel 308 may present visual cues to highlight the locations of the selected cart items so as to guide the user in finding them. Fourth panel 310 may present a user workspace for entering or modifying data.

Returning to FIG. 2, at 204, BCMA application 121 enables Bluetooth discovery mode and automatically pairs with an RFID tracking tag 126 attached to the code cart 122. Alternatively, the code cart 122 may be identified by scanning a barcode tag 126 attached to the code cart 122. BCMA application 121 communicates the unique cart identifier retrieved from the tracking tag 126 to the EHR system 106 and receives code cart data associated with the code cart 122. Such code cart data may include any updates on any cart items (e.g., medications) that may have expired. At 206, BCMA application 121 determines if there are any expired cart items in the code cart 122. In response to a determination that there is at least one expired cart item, at 208, BCMA application 121 presents an alert notification via user interface 119. If there are no expired cart items, method 200 proceeds to 210.

At 210, BCMA application 121 presents a user interface 119 that is ready for cart items to be scanned. For example, BCMA application 121 may present at least fourth panel 310 that includes a user workspace configured to display information retrieved by scanning tracking tags 126 attached to the cart items.

At 212, BCMA application 121 determines if the user has selected a clinical protocol. The user may select an on-screen clinical protocol (e.g., ACLS algorithm) via first panel 304. If the user does not select a protocol, at 214, BCMA application 121 determines if a recommendation of a protocol is to be sent. The user may request for a recommendation of a protocol based on data received from interfaced medical devices 127. If the user declines the recommendation, the method continues at 220. If a recommendation is generated or a user selects a protocol, at 218, BCMA application 121 highlights cart items that may be required based on the selected or recommended protocol.

At 220, BCMA application 121 receives user selections of the cart items. As discussed previously, cart items may include medications 123 and/or equipment 124. The user may select the desired cart item via the user interface 119 (e.g., fourth panel 310), and then scan, using data collector 120 (e.g., barcode scanner), the tracking tag 126 physically attached to the cart item. The user interface 119 (e.g., third panel 308) may display the location of the cart item within the code cart 122 in response to the user selection. Alternatively, the user may make the selection simply by scanning, using the data collector 120, the tracking tag 126 attached to the cart item. Scanning during Code-Mode only requires a single scan of each tracking tag 126, similar to scanning in a grocery store.

At 224, BCMA application 121 provides visual confirmation of the selection. In some implementations, as each tracking tag 126 attached to the cart item is scanned, a visual image of that cart item is presented on the user interface 119 to serve as a visual confirmation that the desired cart item was selected. BCMA application 121 may also present an alert notification via the user interface 119 if a mismatch between the cart item selected via the user interface 119 and the cart item that has been physically removed from the code cart 122 is found (e.g., different NDC numbers). In some implementations, if the cart item is a medication, fourth panel 310 may present dosage fields that are pre-populated with values after scanning the tracking tag 126. Alternatively, the dosage fields may be pre-populated with recommended dosages for the specific clinical situation based on the selected protocol. The user may modify or revise the field values subsequently.

At 226, BCMA application 121 updates the medical emergency record. The medical emergency record documents all events, interventions, cart items, etc., used during the medical emergency. The medical emergency record information may be displayed in the code blue documentation form presented by second panel 306 of the user interface 119. The updating of the medical emergency record may be performed as the tracking tag 126 of each cart item is scanned. As each tracking tag is scanned and documented in, for example, fourth panel 310, information associated with the cart item may also be displayed in the medical emergency documentation form as displayed by second panel 306 of the user interface 119. Information associated with the cart item may include, for example, the administered dosage and time of scanning. Such information may be retrieved from the tracking tag 126 or code cart data stored by the EHR system 106.

Additional information of interventions made during the medical emergency may also be recorded in the medical emergency record. Such information may be automatically derived from data captured by medical devices connected to the EHR system 106, or received by data collector 120 at the workstation 118 (e.g., scanned tracking tags attached to cart items). For example, a user may remove a laryngoscope and blade from the code cart 122 and scan, using data collector 120, the tracking tags 126 attached to them. BCMA application 121 may then document the fact that the patient was intubated on the medical emergency record. In another example, the defibrillator on the code cart 122 may be connected to the data collector 120. Each time a shock is delivered via the defibrillator, the data collector 120 receives a signal, and the BCMA application 121 documents, in the medical emergency record, the time of receipt and the fact that defibrillation has been administered. Alternatively, such information may be manually provided by the user via the code documentation form presented by second panel 306. If anything has changed as a result of the patient's condition, the form may be edited after the medical emergency has concluded.

Clinical data acquired by medical devices 127 during the medical emergency may be integrated into a single longitudinal medical emergency record. Documentation of all medications, equipment, procedures, defibrillation, EKG tracing, ventilator readings, audio/video recordings, etc., associated with the medical emergency may be merged into a single time-based view of the medical emergency record for an exact account of each intervention. For example, the time-based view may include information pertaining to EKG tracings combined with medication administration activities and other interventions (e.g., defibrillation) administered, as well as any additional documentation of interventions inferred based on cart items scanned during the medical emergency.

BCMA application 121 may be pre-configured to make recommendations during the course of the medical emergency based on, for example, physiologic data received from interfaced medical devices 127 or the sequence in the protocol. BCMA application 121 may employ clinical decision support tools to advise or recommend treatment during the medical emergency. For example, BCMA application may automatically generate a suggestion to administer 150 mg dose of amiodarone IV bolus for ventricular tachycardia with a pulse, and 300 mg dose for pulseless ventricular tachycardia or ventricular fibrillation. As such, data received from the electrocardiogram (ECG or EKG) monitor or other medical devices 127 may be used to automatically generate a recommendation for treatment.

Par levels for any cart item may also be pre-configured during system set-up. If, during the course of a medical emergency, a medication or equipment reaches the minimum set par level, a critical notification may be electronically sent to the user interface 134 at the medical supplier system 132 for immediate re-stocking or replenishment. Pharmacies and/or hospital supply departments that supply items to stock the code cart 122 may also use the user interface 134 to track the stock, manage inventory and expiration dating, track the code cart movement within the hospital or organization, and so forth.

Once the medical emergency is complete, the user completes and saves the medical emergency record and exits Code Mode. The used code cart 122 may be removed from the current nursing station location unit and assigned to a Pharmacy or Central Supply area. EHR system 106 may automatically update the location of the used code cart, and generate a request for a replacement cart to be delivered to the current nursing unit. EHR system 106 may further generate or initiate the generation of an invoice to charge the patient for all cart items used during the medical emergency. In some implementations, analytics or business intelligence is used to review the medical emergency record generated during the medical emergency. The medical emergency record may be reviewed to determine, for example, competencies, compliance or variance from ACLS or other clinical protocols or guidelines.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A medical emergency system, comprising:
a code cart with tracking tags attached to the code cart and cart items; and
a computer system paired with the code cart, wherein the computer system includes a data collector for scanning the tracking tags and an application, wherein the application is executable by a processor to perform steps for facilitating a medical emergency workflow, the steps comprising:
receiving a request for a clinical protocol based on data received from at least one medical device interfaced with the code cart;
generating, in response to the request, a recommendation of at least one clinical protocol;
highlighting one or more cart items required by the at least one recommended clinical protocol;
receiving, from the data collector, information associated with one or more selected cart items during a code event; and
updating a medical emergency record based at least in part on the received information.

2. The system of claim 1, further comprising: automatically pairing the code cart with the computer system.

3. The system of claim 1, wherein the tracking tags are at least one of barcode tags or radio-frequency identification (RFID) tags.

4. The system of claim 1, wherein the data collector comprises at least one of a barcode scanner or a RFID reader.

5. The system of claim 1, wherein the tracking tags are uniquely associated with the code cart and the cart items.

6. The system of claim 1, further comprising: receiving, from the data collector, information associated with the code cart and at least one selected cart item.

7. The system of claim 1, wherein the computer system is further coupled to an electronic health records (EHR) system configured to store code cart data associated with one or more code carts.

8. The system of claim 7, wherein the code cart data comprises a unique identifier, code cart location, and information associated with the cart items.

9. The system of claim 1, further comprising:
determining at least one cart item is expired; and
presenting an alert notification in response to the determining.

10. The system of claim 1, wherein the medical record is updated based on data captured during the event and merged into a single time-based record of the event.

11. A non-transitory computer storage medium storing computer-useable instructions that, when used by one or more computing devices, cause the one or more computing devices to perform operations comprising:
automatically pairing with a code cart, the code cart comprising one or more cart items, with tracking tags attached to the code cart and cart items;
receiving a selection of a clinical protocol;
highlighting at least one cart item based on the selected clinical protocol;
receiving a selection of at least one cart item;
receiving, from a data collector, information associated with the at least one selected cart items; and
updating a medical emergency record based at least in part on the received information.

12. The non-transitory computer storage medium of claim 11, further comprising:
receive data captured by at least one interfaced medical device;
update the medical emergency record based at least in part on the received data.

13. The non-transitory computer storage medium of claim 12, further comprising generating recommendations for treatment based on the received data captured.

14. The non-transitory computer storage medium of claim 11, further comprising generating a notification based on determining the quantity of a cart item falling below a par level.

15. The non-transitory computer storage medium of claim 11, further comprising providing a visual confirmation for the at least one selected cart items.

16. The non-transitory computer storage medium of claim 11, further comprising providing an alert if there is a mismatch between the selected cart item and received information from the data collector.

17. The non-transitory computer storage medium of claim 11, further comprising:
   receiving code cart data upon pairing with the code cart; and
   determining if any cart items are expired.

18. The non-transitory computer storage medium of claim 17, further comprising providing an alert if it is determined that any cart items are expired.

19. The non-transitory computer storage medium of claim 17, further comprising determining at least one of: the cart contains used equipment or the cart contains items that have reached pre-configured par levels.

20. A computer-implemented method for facilitating a medical emergency workflow, the method comprising:
   automatically pairing a code cart with a computer system in response to initiation of a medical emergency;
   receiving patient information based on patient identification;
   receiving a clinical protocol recommendation based on the received patient information and data received from at least one interfaced medical device;
   highlighting at least one cart item based on the received clinical protocol recommendation;
   updating a medical emergency record into a single time-based record of the medical emergency based on data captured during the event.

* * * * *